United States Patent [19]

Saville

[11] Plant 4,582

[45] Jul. 29, 1980

[54] ROSE PLANT

[76] Inventor: F. Harmon Saville, 58 Hammond St., Rowley, Mass. 01969

[21] Appl. No.: 36,004

[22] Filed: May 4, 1979

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new minature bicolor rose with predominantly red to orange red upper petal surface coloring and bright to buttercup yellow reverse petal surface coloring.

1 Drawing Figure

1

The present invention relates to a new and distinct variety of rose plant of the miniature rose class, which was originated by my crossing as seed parent the rose known as "Sheri Anne" and a rose seedling which is a cross of "Yellow Jewel" x "Tamango" as pollen parent.

Among the novel characteristics possessed by this new variety which distinguish it from its parents and all other varieties of which I am aware are unusual bicolor flowers of good form borne primarily one to a stem in a manner typical of hybrid tea plants; first high centered, then becoming flat upon opening, with petals changing from loosely rolled outward to reflexing at maturity. The novel coloring combines a red to orange-red upper petal surface and a yellow reverse or underside petal surface which is at times buttercup yellow but can be bright yellow. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose with a fast recurring blooming habit and a very vigorous well branched plant. The flowers are well formed, and the plant displays the bicolored flowers extremely well. The color novelty is pleasing and attractively visible at great distances.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "42B" is plate 42B of the Royal Horticultural Society Color Chart.

Parentage: Seedling.

*Seed parent.*—"Sheri Anne".

*Pollen parent.*—"Yellow Jewel" x "Tamango".

Class: Miniature.

The following observations are made of specimens grown in a greenhouse in Essex County, Mass., during the month of December.

FLOWER

Blooming habit: Fast recurring.

2

(1) *Size.*—Medium to large.

(2) *Form.*—Ovate, pointed.

(3) *Color.*—When sepals first divide - Reverse side of petals first seen under sepals have yellow coloring varying from bud to bud but generally 12D to 12B at the base shading to 14C at petal tips; upper surface of petals have yellow coloring at base to about ⅓ of petal where well delineated red to orange-red coloring begins.

(4) *Sepals.*—Relatively smooth, somewhat longer than bud.

(5) *Peduncle.*—Length — about 1 to ¼ inches, good proportion to bloom. Aspect — straight, sturdy. Strength — erect, strong. Color — 143C.

B. Bloom:

(1) *Size.*—Average size when fully expanded — about 1¾ inches.

(2) *Borne.*—Primarily singly (one to a stem).

(3) *Form.*—High centered, at first, becoming flat upon opening, petals remaining loosely rolled outward at first and reflexing at maturity.

(4) *Petalage.*—Number of petals under normal conditions - about 25 to 30.

(5) *Color.*—(During first two days). The bicolor blooms generally have a yellow to yellow-orange reverse and a red to orange-red upper petal surface. The upper petal surface coloring is generally yellow from base of attachment to at most about ⅓ of the petal where generally well delineated red and orange-red coloring begins. The yellowish segment of the upper petal surface is 16B or 16C but can be 14B. The balance of the upper petal surface is orange-red to red e.g. 34A to B or 42B. However, this coloring can be as bright as 42A. The reverse of the petal, i.e., the under side, is generally yellow to yellow-orange. The reverse surface coloring may be 12B at base shading to 16C. At times the color may shade to 11C toward the tip. The general tonality from a distance is brilliant orange-red and gold bicolor.

(6) *Color change.*—As bloom ages — the orange-red color effect is enhanced by the yellow "eye" of the flower center. As the flowers age the red coloring deepens and the yellow becomes paler.

C. Petals:

(1) *Texture.*—Firm and crisp.

(2) *Appearance.*—Inside — velvety; outside — satiny.

(3) *Form.*—Wide, ovate.

(4) *Arrangement.*—Shingle-like.

(5) *Petaloids in center.*—4 to 10.
(6) *Persistence.*—Drop cleanly.
(7) *Fragrance.*—Strong, sweet.
(8) *Lasting quality.*—Long on plant and as cut flower retains color.

REPRODUCTIVE ORGANS

A. Stamens, filaments and anthers:
(1) *Arrangement.*—Regularly arranged around styles
(2) *Color.*—15A.
B. Pollen: Color — 17B.
C. Styles: Even length, normal.
D. Stigmas: Color — 19B.
E. Hips: Shape — spherical, ⅝ inch diameter, color — 30A, seeds do not protrude.

PLANT

A. Form: Compact, spreading.
B. Growth: Very vigorous, well branched. Height attained — 12 to 15 inches.
C. Foliage: Compound 5 to 7 leaflet leaves.
(1) *Size.*—Medium.
(2) *Quantity.*—Abundant.
(3) *Color.*—New foliage: Upper side — 143A. Under side — 148C. Old foliage: Upper side — 139A. Under side — 138B.
(4) *Shape.*—Oval, slightly pointed.

(5) *Texture.*—Upper side - glossy, leathery. Under side — matte.
(6) *Edge.*—Evenly serrated.
(7) *Serration.*—Even and relatively broad point.
(8) *Leaf stem.*—Color — near to 146A. Under side — near to 146C.
(9) *Stipules.*—Moderately long, smooth.
(10) *Resistance to disease.*—Blackspot — good. Mildew — good.
D. Wood
(1) *New wood.*—Color — near 144A. Bark — smooth.
(2) *Old wood.*—Color — near to 139C. Bark — smooth.
E. Thorns:
(1) *Thorns.*—Quantity — ordinary. On laterals from stalk — ordinary. Form — long, thin, pointed, slightly curved downward. Length — long. Color (when young) — 180C. Position — irregular.
(2) *Prickles.*—None.
F. Winter hardiness: Needs ordinary protection.

I claim:

1. A new and distinct variety of rose plant of the miniature class, substantially as shown and described, characterized particularly by unusual bicolor flowers with red to orange-red upper petal surface and yellow to yellow-orange reverse, borne primarily one to a stem on a vigorous plant with attractive foliage.

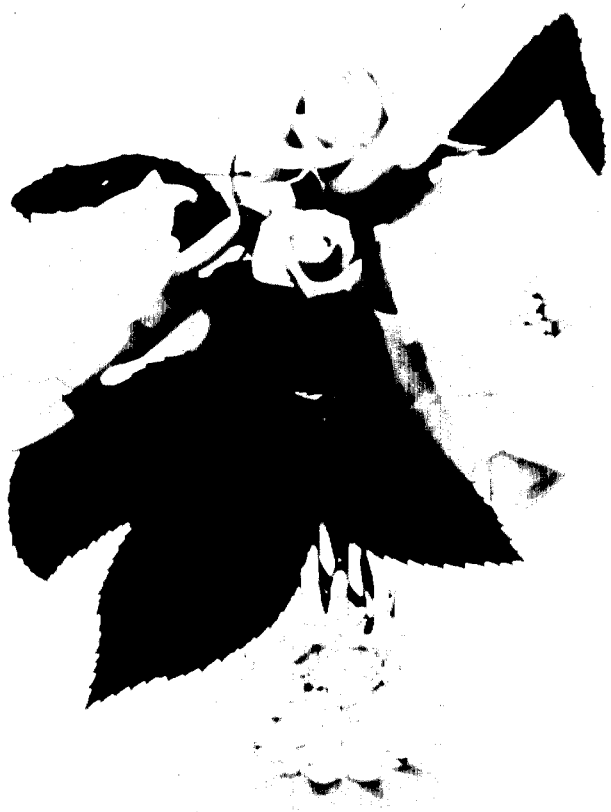

* * * * *